United States Patent [19]
Sherif et al.

[11] Patent Number: 5,824,832
[45] Date of Patent: Oct. 20, 1998

[54] LINEAR ALXYLBENZENE FORMATION USING LOW TEMPERATURE IONIC LIQUID

[75] Inventors: Fawzy G. Sherif, Stony Point; Lieh-Jiun Shyu, Yorktown Heights; Carl C. Greco, Garnerville, all of N.Y.

[73] Assignee: Akzo Nobel NV, Arnhem, Netherlands

[21] Appl. No.: 827,127

[22] Filed: Mar. 27, 1997

Related U.S. Application Data

[63] Continuation-in-part of Ser. No. 681,338, Jul. 22, 1996, Pat. No. 5,731,101.

[51] Int. Cl.$^6$ .................................................... C07C 2/64
[52] U.S. Cl. .................. 585/455; 585/456; 585/459; 585/461; 585/462; 585/469; 556/2; 556/138
[58] Field of Search ........................ 585/455, 459, 585/461, 462, 469, 456; 556/2, 138

[56] References Cited

U.S. PATENT DOCUMENTS

| 5,045,244 | 9/1991 | Marlett | 260/665 G |
| 5,386,072 | 1/1995 | Cozzi et al. | 585/456 |
| 5,731,101 | 3/1998 | Sherif et al. | 429/102 |

FOREIGN PATENT DOCUMENTS

| 576323 | 12/1993 | European Pat. Off. . |
| WO 95/21806 | 8/1995 | WIPO . |
| WO 95/21871 | 8/1995 | WIPO . |
| WO 95/21872 | 8/1995 | WIPO . |
| WO 96/20905 | 7/1996 | WIPO . |

OTHER PUBLICATIONS

Derwent Patent Abstract 89–272569/38 (1989).

M.F. Cox et al., "Effect of LAB Composition on LAS Performance", INFORM, vol. 8, No. 1 (Jan. 1997), pp. 19–24.

M. Matsui et al., "Aluminum Chloride–Tetraalkylammonium Halide Complex as a Novel Catalyst in Friedel–Crafts Alkylation. Direct Construction of the Chroman Structure from 1,3–Diene", Bull. Chem. Soc. Jpn., 68, 2663–2668 (1995). No month available.

*Primary Examiner*—Bruce F. Bell
*Attorney, Agent, or Firm*—Richard P. Fennelly

[57] ABSTRACT

A low temperature molten ionic liquid composition comprising a mixture of a metal halide and an alkyl-containing amine hydrohalide salt can be used in linear alkylbenzene formation. The metal halide is a covalently bonded metal halide which can contain a metal selected from the group comprised of aluminum, gallium, iron, copper, zinc, and indium, and is most preferably aluminum trichloride. The alkyl-containing amine hydrohalide salt may contain up to three alkyl groups, which are preferably lower alkyl, such as methyl and ethyl.

16 Claims, No Drawings

LINEAR ALXYLBENZENE FORMATION USING LOW TEMPERATURE IONIC LIQUID

RELATED APPLICATION

This application is a continuation-in-part of U.S. Ser. No. 08/681,338, filed Jul. 22, 1996, now U.S. Pat. No. 5,731,101, issued Mar. 24, 1998.

BACKGROUND OF THE INVENTION

This invention relates to the catalytic alkylation of an aromatic molecule with a suitable alkylating reagent (e.g., a $C_8$ to $C_{18}$, such as a $C_4$ to $C_{14}$ olefin or a halogenated alkane of similar chain length) using, as the catalyst, a composition which is molten at low temperatures. The term "linear alkylbenzene formation" as used herein is intended to cover the process by which higher alkyl moieties are placed on benzene compounds, with the term "alkyl" being intended to cover the conventional paraffinic alkane substituents, "higher" being intended to mean $C_4$ or longer, preferably $C_8$ or longer, and the "benzene" including both unsubstituted as well as substituted (e.g., lower alkyl-substituted) benzene compounds. As is well known in the art, this process is practiced by the catalytic reaction of an unsubstituted or lower alkyl-substituted benzene compound with a higher alkene or a halo-substituted higher alkane, such as a chloro-substituted higher alkane. In commercial practice, the alkylating agent is one or more a long chain alkene or halogenated alkane, such as dodecylchloride or dodecene. Recent patents which illustrate an alkylation reaction of this type include U.S. Pat. Nos. 5,196,574 to J. A. Kocal and 5,386,072 to P. Cozzi et al. A recent publication discussing this reaction is contained in INFORM, Vol. 8, No. 1 (Jan. 1997), pp. 19–24.

A class of ionic liquids which is of special interest to this invention is the class of fused salt compositions which are molten at low temperature. Such compositions are mixtures of components which are liquid at temperatures below the individual melting points of the components. The mixtures can form molten compositions simultaneously upon contacting the components together, or after heating and subsequent cooling.

Examples of conventional low temperature ionic liquids or molten fused salts are the chloroaluminate salts discussed by J. S. Wilkes, et al., J. Inorg. Chem., Vol. 21, 1263–1264, 1982. Alkyl imidazolium or pyridinium salts, for example, can be mixed with aluminum trichloride ($AlCl_3$) to form the fused chloroaluminate salts. Also, chlorogallate salts made from gallium trichloride and methylethyl-imidazolium chloride are discussed in Wicelinski et al., "Low Temperature Chlorogallate Molten Salt Systems," J. Electrochemical Soc., Vol. 134, 262–263, 1987. The use of the fused salts of 1-alkylpyridinium chloride and aluminum trichloride as electrolytes are discussed in U.S. Pat. No. 4,122,245. Other patents which discuss the use of fused salts from aluminum trichloride and alkylimidazolium halides as electrolytes are U.S. Pat. Nos. 4,463,071 and 4,463,072 and British Patent No. 2,150,740. Unfortunately, the alkylimidazolium salts are difficult to prepare, and the alkyl pyridinium salts can be too easily reduced.

U.S. Pat. No. 4,764,440 to S. D. Jones describes ionic liquids which comprise a mixture of a metal halide, such as aluminum trichloride, and what is termed a "hydrocarbyl-saturated onium salt", such as trimethylphenylammonium chloride. In such ionic liquids, the onium salt component, if based on the presence of a nitrogen atom, is fully saturated with four substituent groups.

U.S. Pat. No. 5,104,840 to Y. Chauvin et al. describes ionic liquids which comprise at least one alkylaluminum dihalide and at least one quaternary ammonium halide and/or at least one quaternary ammonium phosphonium halide; and their uses as solvents in catalytic reactions.

PCT International Patent Publication No. WO 95/21872 describes ternary ionic liquids which can comprise a metal halide, such as aluminum trichloride, an imidazolium or pyridinium halide, and a hydrocarbyl substituted quaternary ammonium halide or a hydrocarbyl substituted phosphonium halide. See page 4, lines 18–24 for the description of the hydrocarbyl substituted quaternary ammonium halide.

In view of the disadvantages of known compositions, it would be desirable to have fused salt compositions which would not be difficult to prepare, which would be useful, for example, as a catalyst in alkylation and polymerization reactions and as solvents for chemical and electrochemical processes, and which would be formed using relatively low cost components as compared to the ionic liquids of the prior art.

U.S. Pat. No. 5,731,101 describes and claims the type of ionic liquid composition intended for use herein.

SUMMARY OF THE INVENTION

This invention relates to linear alkylbenzene formation using, as the catalyst, a low temperature molten composition comprising a mixture of a metal halide and an alkyl-containing amine hydrohalide salt.

DETAILED DESCRIPTION OF THE INVENTION

The low temperature molten compositions, or ionic liquids, which are used as catalysts in this invention can be referred to as fused salt compositions, or ionic aprotic solvents. By "low temperature molten" is meant that the compositions are in liquid form below about 100° C. at standard pressure. Preferably, the molten composition is in liquid form below about 60° C., and more preferably below about 30° C. at standard pressure.

The metal halides useful in this invention are those compounds which can form anions containing polyatomic chloride bridges in the presence of the alkyl-containing amine hydrohalide salt. Preferred metal halides are covalently bonded metal halides. Suitable metals which can be selected for use herein include those from Groups VIII and IB, IIB and IIIA of the Periodic Table of the Elements. Especially preferred metals are selected from the group comprising aluminum, gallium, iron, copper, zinc, and indium, with aluminum being most preferred. The corresponding most preferred halide is chloride and therefore, the most preferred metal halide is aluminum trichloride. Other possible choices for metal halides to select include those of copper (e.g., copper monochloride), iron (e.g., ferric trichloride), and zinc (e.g., zinc dichloride). Aluminum trichloride is most preferred because it is readily available and can form the polynuclear ion having the formula $Al_2Cl_7^-$. Furthermore, the molten compositions comprising this polynuclear ion are useful as described hereinbefore. Mixtures of more than one of these metal halides can be used.

Granular (+4 −14 mesh) aluminum trichloride is an especially preferred metal halide to employ. It is easy to handle in air without fuming problems and has good flow properties. Its reaction with trimethylamine hydrochloride, for example, is slower and more uniform than with aluminum trichloride powder, with a temperature exotherm to about 150° C. While the resulting ionic liquid is slightly hazy due to the presence of insoluble impurities from the aluminum trichloride, the insoluble, which settle out upon storage of the liquid, do not have an adverse effect on the catalytic performance of the ionic liquid in regard to the process of the present invention.

The terminology "alkyl-containing amine hydrohalide salt", as used herein, is intended to cover monoamines, as well as diamines, triamines, other oligoamines and cyclic amines which comprises one or more "alkyl" groups and a hydrohalide anion. The term "alkyl" is intended to cover not only conventional straight and branched alkyl groups of the formula —$(CH_2)_nCH_3$ where n is from 0 to about 29, preferably 0 to about 17, in particular 0 to 3, but other structures containing heteroatoms (such as oxygen, sulfur, silicon, phosphorus, or nitrogen). Such groups can carry substituents. Representative structures include ethylenediamine, ethylenetriamine, morpholino, and poloxyalkylamine substituents. "Alkyl" includes "cycloalkyl" as well.

The preferred alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. The preferred compounds that are contemplated herein have the generic formula $R_3N.HX$, where at least one of the "R" groups is alkyl, preferably alkyl of from one to eight carbon atoms (preferably, lower alkyl of from one to four carbon atoms) and X is halogen, preferably chloride. If each of the three R groups is designated $R_1$, $R_2$ and $R_3$, respectively, the following possibilities exist in certain embodiments: each of $R_1$–$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. Most preferably, these groups are methyl or ethyl groups. If desired the di- and trialkyl species can be used. One or two of the R groups can be aryl, but this is not preferred. The alkyl groups, and aryl, if present, can be substituted with other groups, such as a halogen. Phenyl and benzyl are representative examples of possible aryl groups to select. However, such further substitution may undesirably increase the size of the group, and correspondingly increase the viscosity of the melt. Therefore, it is highly desirable that the alkyl groups, and aryl, if present, be comprised of carbon and hydrogen groups, exclusively. Such short chains are preferred because they form the least viscous or the most conductive melts. Mixtures of these alkyl-containing amine hydrohalide salts can be used.

The mole ratio of alkyl-containing amine hydrohalide salt to metal halide can, in general, range from about 1:1 to about 1:2.5. In a highly preferred embodiment, the low temperature molten composition useful as a catalyst in this invention consists essentially of the metal halide and the alkyl-containing amine hydrohalide salt.

Specifically, the most preferred low temperature molten composition is a mixture consisting essentially of a mole ratio of trimethylamine hydrochloride to aluminum trichloride of from about 1:1.5 to about 1:2, preferably about 1:2.

Typically, the metal halide and the alkyl-containing amine hydrohalide salt are solids at low temperature, i.e., below about 100° C. at standard pressure. After mixing the two solids together, the mixture can be heated until the mixture becomes a liquid. Alternatively, the heat generated by the addition of the two solids will result in forming a liquid without the need for additional external heating. Upon cooling, the mixture remains a liquid at low temperature, i.e., below about 100° C., preferably below about 60° C., and more preferably below about 30° C.

The process of the present invention has a number of advantages as compared to the conventional manner in which linear alkyl benzenes are synthesized in commercial practice. For example, while the use of aluminum chloride, as a catalyst, at a desirable catalyst/olefin mole ratio (for example, about 0.12), will yield a product having a desirable content for a liquid detergent composition (greater than about 30%) of 2-dodecyl benzene, the process involves solid materials handling, and an undesired sludge by-product is formed. The present invention uses a similar catalyst olefin ratio, does not involve solid materials handling, and does not form an undesired sludge by-product. The use of hydrogen fluoride, as the catalyst, at a much higher catalyst/olefin ratio (about 5–20), while not causing a sludge problem or requiring solid materials handling and while being intermediate in regard to its dialkyl benzene impurity level (about 2% or less), results in an inferior content for a liquid detergent composition (about 20%) of 2-dodecyl benzene.

The following isomer distribution (weight % of dodecylbenzene from the reaction of 1-dodecene and benzene) was reported for the two catalyst systems described below:

| Isomers | Catalyst System | |
| --- | --- | --- |
|  | HF | $AlCl_3$ |
| 1-dodecylbenzene | 0 | 0 |
| 2-dodecylbenzene | 20 | 32 |
| 3-dodecylbenzene | 17 | 22 |
| 4-dodecylbenzene | 16 | 16 |
| 5-dodecylbenzene | 23 | 15 |
| 6-dodecylbenzene | 24 | 15 |

The ionic liquid of the present invention is both easily recyclable while the standard HF catalyst that is employed, which has similar features, has recognized environmental shortcomings and needs to be used in higher amounts (a 5 to 20 catalyst/olefin mole ratio) than the present catalyst (about a 0.004 or higher catalyst/olefin mole ratio is generally needed). The present catalyst is a liquid, unlike aluminum trichloride which forms a sludge by-product may be difficult to recycle.

It has been found that the presence of water in the benzene reagent used in the practice of the present invention as well as the composition of the ionic liquid (for example, either 1:2 or 1:1.5 trimethylammonium chloride:aluminum trichloride) does not have a significant effect on the alkylation reaction of this invention. Higher benzene to olefin (dodecene) mole ratios (for example, 12/1 rather than 8/1) produce a higher selectivity to the desired monoalkylbenzene product (namely, 90% versus 80%). Dilution of the reaction medium with paraffins (for example, a threefold dilution) produces a low reaction rate and a low selectivity (for example, 78%) to the desired monoalkylbenzene product.

Besides using the conventional alkylating reagents previously mentioned (e.g., a $C_4$ to $C_{14}$ olefin or a halogenated alkane of similar chain length) in the process of the present invention, this invention contemplates the possible presence of functional groups, such as cyano or halo, on the alkylating agent (e.g., an olefin). In selecting the desired functional group, the chosen group should not be one which will react with the ionic liquid under the particular process conditions used. For example, such groups as hydroxy, amino, and carboxy have been found to react with a metal halide, such as aluminum chloride, under certain process conditions.

The following Examples are illustrations and not limitations of the invention.

EXAMPLE 1

Two moles of aluminum trichloride (266.7 g) were added slowly to one mole of stirred trimethylamine hydrochloride salt (95.57 g), both from Aldrich Chemical Co., under a blanket of dry air. The reaction was exothermic. A light brown liquid was formed. This liquid was stirred for one hour, and the liquid had a density of 1.4–1.5 g/cc at room temperature. The product was stable as a liquid at room temperature under a dry atmosphere. When cooled, it changed to a glassy viscous mass at –10° C. On warming to room temperature, it changed back to a flowable liquid.

EXAMPLE 2

This Example is similar to Example 1 with the exception that the experiment was scaled up using a commercially available 70% aqueous solution of trimethylamine hydrochloride (Akzo Nobel Chemicals Inc.). A 200 g portion of the solution (170 cc) was evaporated in a porcelain dish until 60% of the liquid had evaporated. The slurry that formed was then introduced into a flask and was treated with low vacuum using an aspirator until all of the moisture had been removed. The solid was then mixed with two mole equivalents of aluminum trichloride in two steps. Half of the aluminum trichloride was slowly added with stirring. An exotherm occurred, and a brown liquid was formed. The second half of the aluminum trichloride was then added, and a final liquid was formed which stayed liquid at room temperature. The product was analyzed for its elemental composition. It had the formula $(CH_3)_3NH.Al_2Cl_7$. The results of the analysis are as follows: %Al—14.65% (Found), 14.90% (Calculated); %Cl—67.5% (Found), 68.53% (Calculated); %C—10.1% (Found), 9.94% (Calculated); %H—1.0% (Found), 2.76% (Calculated); and %N—4.0% (Found), 3.87% (Calculated). The nuclear magnetic resonance spectra of aluminum showed that the aluminum was present as the heptachloroaluminate anion.

EXAMPLE 3

This Example shows the alkylation of benzene to produce linear fatty alkyl benzene using the ionic liquid made in Example 1.

Five grams of dodecene and 30 g of benzene were weighed into a 3-neck flask. The liquids were heated to 80° C. in a nitrogen atmosphere. A few samples were withdrawn before (time 0) and after the addition of 0.04 g of the ionic liquid made in Example 1. The samples were analyzed by GC and the results are shown below:

| SAMPLE | TIME (MIN) | $C_6H_6$ | DODECENE | $C_6H_5C_{12}$* |
|---|---|---|---|---|
| A | 0 | 85.7 | 14.3 | 0 |
| B | 1 | 65.6 | 6.2 | 28.6 |
| C | 15 | 62.9 | 0.1 | 36.2 |
| D | 60 | 72.3 | 0 | 27.6 |

*a mixture of dodecyl benzenes was used.

The conversion of dodecene at 80° C. in the excess of benzene was 100% after fifteen minutes of reaction.

EXAMPLE 4

This Example illustrates the preparation of another ionic liquid useful as a catalyst in linear benzene alkylation.

An ionic liquid comprising triethylamine hydrochloride and aluminum trichloride was prepared by introducing triethylamine hydrochloride(2.3 g, 16.7 mmol) into a flask and then introducing the aluminum trichloride (4.4 g, 33.4 mmol) from a dosing funnel. The reaction mixture immediately became sticky and, when approximately 50% of the aluminum trichloride had been added, it became completely fluid and brownish in color. The reaction was exothermic, and the temperature was kept at 30° C. with the use of an ice bath. When all of the aluminum trichloride had been added, the product was slightly brownish in color and remained fluid at room temperature. The ionic liquid stayed in fluid liquid form until cooled to 0° C. at which point it started to become a viscous composition and eventually a glassy material (at about –20° C.).

EXAMPLE 5

This Example illustrates the preparation of another ionic liquid useful as a catalyst in linear benzene alkylation.

Another ionic liquid was formed by introducing dibutylamine hydrochloride (2.5 g, 15.1 mmol) into a flask and then introducing the aluminum trichloride (4.0 g, 30.0 mmol) from a dosing funnel. The reaction mixture immediately became sticky and, when approximately 50% of the aluminum trichloride had been added, it became completely fluid and brownish in color. The reaction was exothermic, and the temperature was kept at 30° C. with the use of an ice bath. When all of the aluminum trichloride had been added the product was slightly brownish in color and remained fluid at room temperature. The ionic liquid stayed in fluid liquid form until cooled to 0° C. at which point it started to become a viscous composition and eventually a glassy material (at about –20° C.).

EXAMPLE 6

This Example illustrates the preparation of another ionic liquid useful as a catalyst in linear benzene alkylation.

Yet another ionic liquid was formed by introducing ethylamine hydrochloride (3.0 g, 36.8 mmol) into a flask and then introducing the aluminum trichloride (9.8 g, 73.6 mmol) from a dosing funnel. The reaction mixture became sticky when approximately 50% of the aluminum trichloride had been added. When all of the aluminum trichloride had been added the product was completely fluid and brownish in color. The reaction was exothermic, and the temperature was kept at 40° C. with the use of an ice bath. The mixture solidified below 35° C.

EXAMPLE 7

This Example illustrates the preparation of another ionic liquid useful as a catalyst in linear benzene alkylation.

Yet another ionic liquid was formed by introducing dibutylamine hydrochloride (2.4 g, 14.6 mmol) into a flask and then introducing ferric trichloride (4.7 g, 29.2 mmol) from a dosing funnel. The reaction mixture immediately became sticky and, when approximately 50% of the ferric trichloride had been added, it was completely fluid and deep brown to black in color. The reaction was exothermic. When all of the ferric trichloride had been added, the product was brown/black in color and solidified below 45° C.

EXAMPLE 8

This Example illustrates the preparation of another ionic liquid useful as a catalyst in linear benzene alkylation.

This Example is similar to Example 1, except that the metal halide was $FeCl_3$. When 9.6 g of trimethylammonium chloride, 0.1 mole, was mixed with 32.4 g of FeCl$_3$ (0.2 mole) and warmed to 40° C., a reaction took place accompanied by an exotherm to about 70° C. A liquid was formed. The liquid was viscous at room temperature but very flowable above 50° C.

EXAMPLE 9

This Example illustrates the preparation of another ionic liquid useful as a catalyst in linear benzene alkylation.

This Example is similar to Example 1, except that the metal halide was ZnCl$_2$. When 9.6 g of trimethylammonium chloride, 0.1 mole, was mixed with 27.2 g of ZnCl$_2$, 0.2 mole, and heated to 100° C., a transparent colorless liquid was formed. Below this temperature, the material was transformed to a transparent glassy solid.

EXAMPLE 10

This Example illustrates the preparation of another ionic liquid useful as a catalyst in linear benzene alkylation.

This Example is similar to Example 1, except that the metal halide was CuCl. When 9.6 g of trimethylammonium chloride, 0.1 mole, was mixed with 19.8 g of CuCl, 0.2 mole, and heated to 50° C., a brown liquid was formed. The material stayed as a liquid above this temperature.

EXAMPLES 11–13

These Examples illustrate the attempts at the preparation of a basic ionic liquid, a neutral ionic liquid, and an acidic ionic liquid. Only the acidic material was obtainable.

In all the preparations, a three necked round bottom flask (50 mL) equipped with a nitrogen inlet and outlet, a thermometer and a dropping funnel with a large dosing opening, and a magnetic stirring bar were employed. All operations were carried out under a nitrogen atmosphere.

"Basic ionic liquid"

Dimethylamine hydrochloride (2.07 g, 25.4 mmol) was introduced into the flask, and AlCl$_3$ (1.7 g, 12.7 mmol) was added from the dropping funnel. When all the AlCl$_3$ had been added, the reaction mixture became light brown and sticky. The flask which contained the product mixture was placed in an oil bath and warmed slowly. When the temperature of the oil bath was above the 120° C., HCl gas was formed, and the product decomposed. No ionic liquid was formed using these concentrations of the reagents and these conditions.

"Neutral ionic liquid"

Dimethylamine hydrochloride (2.06 g, 25.4 mmol) was introduced into the flask, and AlCl$_3$ (3.3 g, 24.7 mmol) was added from the dropping funnel. The addition of AlCl$_3$ was done rapidly, and the reaction was exothermic. When all the AlCl$_3$ had been added, the reaction mixture became light brown and liquid. When the reaction mixture was cooled to room temperature, it became a solid. The melting point of the reaction mixture was measured and was found to be 88° C.

"Acid ionic liquid"

Dimethylamine hydrochloride (1.96 g, 24 mmol) was introduced into the flask, and AlCl$_3$ (6.5 g, 48.8 mmol) was added from the dropping funnel. The addition of AlCl$_3$ was done rapidly, and the reaction was exothermic. When all the AlCl$_3$ had been added, the reaction mixture became light brown and liquid. When the reaction mixture was cooled to room temperature, it became a solid. The melting point of the reaction mixture was measured and was found to be 34° C.

EXAMPLE 14

This Example shows the alkylation of benzene to produce a linear fatty alkyl benzene using the ionic liquid made in Example 2.

First, 24.04 g of benzene and 4.24 g of dodecene were weighed into a 3-neck flask. The mixture was then fluxed at 80° C. under a nitrogen atmosphere. A sample was taken and was analyzed by GC. It showed that no reaction had taken place. Two minutes after addition of 1.85 g of the ionic liquid from Example 2 with similar heating, a sample was again taken and was analyzed by GC. It showed that dodecene had been converted to mono- and poly-dodecyl benzenes with 93% activity and 95% selectivity to mono-dodecyl benzene. The weight distribution of mono-dodecyl benzene isomers is given below:

| | |
|---|---|
| 2-dodecyl benzene | 31.9% |
| 3-dodecyl benzene | 18.6% |
| 4-dodecyl benzene | 15.7% |
| 5- & 6-dodecyl benzene | 32.5% |

The mixture was stirred at 80° C. for an hour and was cooled to room temperature overnight. To demonstrate that the ionic liquid catalyst was reusable, 4.27 g of dodecene was added to the remaining solution containing the ionic liquid. The temperature increased to 43° C. indicating that a rapid alkylation reaction took place. A sample was taken four minutes after the addition of dodecene. It showed that dodecene was 92% converted with 89% selectivity to mono-dodecyl benzene.

The organic layer was subsquently separated from the ionic liquid.

To further demonstrate the activity of the used ionic liquid, it was added to a freshly prepared solution of benzene (23.28 g) and dodecene (6.27 g). The temperature increased to 47° C. A sample was analyzed, and it was found that dodecene had been 99% converted with 91% selectivity to mono-dodecyl benzene.

EXAMPLE 15

This Example also shows the alkylation of benzene to produce linear fatty alkyl benzene using the ionic liquid made in Example 2.

First, 20.08 g of benzene and 5.39 g of dodecene were weighed into a 3-neck flask. The mole ratio of benzene to dodecene was 8:1. The flask was kept in an ice bath and was maintained at 0° C. A smaple was taken and analyzed by GC. It shows that there had been no alkylation reaction. Two minutes after addition of 1.2 g of ionic liquid, the temperature increased to 30° C., a sample was taken and was analyzed by GC. It showed that dodecene had been converted to mono- and poly-dodecyl benzenes with 95% activity and 90% selectivity to mono-dodecyl benzene. The weight distribution of mono-dodecyl benzene isomers is given below:

| | |
|---|---|
| 2-dodecyl benzene | 35.8% |
| 3-dodecyl benzene | 18.9% |
| 4-dodecyl benzene | 15.0% |
| 5- & 6-dodecyl benzene | 30.1% |

EXAMPLE 16

In this Example, the procedure used in Example 2 was followed and 18 g of ionic liquid was prepared and placed at the bottom of a tube reactor. The reactor was kept at room temperature. A solution of 34.9 g of benzene mixed with 9.4 g of dodecene was then placed in a reservoir on top of the tube reactor. The mixed solution was bubbled through the ionic liquid at room temperature at an addition rate of 2 ml/min. After all the mixed solution had passed through the ionic liquid, it was analyzed by GC. This solution was recycled six times, with the conversion of dodecene to mono- and poly-dodecyl benzenes being shown below after each cycle:

| Cycle 1 | 19% |
| Cycle 2 | 50% |
| Cycle 3 | 72% |
| Cycle 4 | 90% |
| Cycle 5 | 89% |
| Cycle 6 | 97% |

The weight distribution of mono-dodecyl benzene isomers in the sample after the sixth cycle is given below:

| 2-dodecyl benzene | 37.9% |
| 3-dodecyl benzene | 19.2% |
| 4-dodecyl benzene | 14.2% |
| 5- & 6-dodecyl benzene | 27.9% |

EXAMPLE 17

A 70% aqueous solution of trimethylamine hydrochloride salt, from Akzo Nobel Chemicals Inc., was used to prepare anhydrous trimethylamine hydrochloride salt. Two moles of aluminum trichloride, from Durham Chemicals, was then added slowly to one mole of the thus prepared anhydrous trimethylamine hydrochloride salt, with stirring. The reaction was exothermic. A grey-color liquid was formed. Some fine insoluble solid was observed suspending in the liquid. This liquid was used as a catalyst for the following benzene alkylation to make linear alkyl benzene.

In the alkylation reaction, 30.2 g of benzene and 5.4 g of dodecene were weighed into a 3-neck flask. The mole ratio of benzene to dodecene was 12:1 with the flask being kept in an ice bath. A sample was taken and was analyzed by GC. It showed that there had been no alkylation reaction. Two minutes after addition of 1.3 g of ionic liquid, a sample was again taken and was analyzed by GC. It showed that dodecene had been completely converted (100% conversion) to mono- and poly-dodecyl benzenes at a 78% selectivity to mono-dodecyl benzene. The weight distribution of mono-dodecyl benzene isomers is shown below:

2-dodecyl benzene: 46.1%

3-dodecyl benzene: 19.9%

4-dodecyl benzene: 12.1%

5- and 6-dodecyl benzene: 21.8%

EXAMPLE 18

A 70% aqueous solution of trimethylamine hydrochloride salt, from Akzo Nobel Chemicals Inc., was used to prepare anhydrous trimethylamine hydrochloride salt. One and half moles of aluminum trichloride, from Durham Chemicals, was then added slowly to one mole of the thus prepared anhydrous trimethylamine hydrochloride salt, with stirring. The reaction was exothermic. A grey-color liquid was formed. Some fine insoluble solid was observed suspending in the liquid. This liquid became solid after overnight-standing at room temperature. It was gently heated to become liquid and used as a catalyst for the following benzene alkylation to make linear alkyl benzene.

In the alkylation reaction, 26.7 g of benzene and 7.2 g of dodecene were weighed into a 3-neck flask. The mole ratio of benzene to dodecene was 8:1. The flask was kept at room temperature. A sample was taken and analyzed by GC. It showed that there had been no alkylatuion reaction. Two minutes after addition of 0.46 g of ionic liquid, a sample was again taken and was analyzed by GC. It showed that dodecene had been converted to mono- and poly-dodecyl benzenes with 98% conversion and 87% selectivity to mono-dodecyl benzene. The weight distribution of mono-dodecyl benzene isomers is shown below:

2-dodecyl benzene: 39.1%

3-dodecyl benzene: 19.1%

4-dodecyl benzene: 13.6%

5- and 6-dodecyl benzene: 28.2%

EXAMPLE 19

This Example shows the alkylation of toluene with an alkylating agent carrying a functional group (oleonitrile) to produce tolylstearonitrile using the ionic liquid made in Example 1.

Into a 250 ml flask was added 40 g of the ionic liquid made in Example 1 (0.11 mole) and 100 ml of toluene. To this was added 29 g of oleonitrile (0.11 mole) over a twenty minute period at room temperature. After the addition, the reaction was heated to 80° C. and was maintained at this temperature for three hours. The reaction was distilled to remove excess toluene. Then, 250 ml. of heptane was added with vigorous stirring. The layers that formed were separated (heptane layer on top and ionic layer on the bottom). The heptane layer was washed with water and was then distilled to collect the product as an undistillable residue. The residue was analyzed to be the desired product, tolylstearonitrile, in 70% yield and 80% purity. The ionic liquid layer was treated with 7.3 g of aluminum chloride (0.055 mole) and was used again in the same reaction with fresh oleonitrile and toluene. Workup by the same procedure, as described above, resulted in a yield of 54% for the desired product (tolylstearonitrile).

The preceding Examples are presented for illustrative purposes only and, for that reason, should not be construed in a limiting sense. The scope of protection sought is set forth in the claims which follow.

We claim:

1. A process for linear alkylbenzene formation involving the reaction of a higher alkylating moiety with a benzene compound using, as a catalyst, a low temperature molten ionic liquid composition comprising a mixture of a metal halide and an alkyl-containing amine hydrohalide salt.

2. The process of claim 1 wherein the metal halide is a covalently bonded metal halide.

3. The process of claim 2 wherein the metal of the metal halide is selected from the group consisting of aluminum, gallium, iron, copper, zinc, and indium.

4. The process of claim 3 wherein the metal halide is aluminum trichloride.

5. The process of claim 1 wherein the alkyl-containing amine hydrohalide salt contains three alkyl groups.

6. The process of claim 1 wherein the ionic liquid composition has a mole ratio of the alkyl-containing amine hydrohalide salt to metal halide of from about 1:1 to about 1:2.5.

7. The process of claim 1 wherein the alkyl-containing amine hydrohalide salt is of the formula $R_3N.HX$ where at least one R group is alkyl.

8. The process of claim 7 wherein the alkyl-containing amine hydrohalide salt is of the formula $R_3N.HX$ where at least one R group is alkyl and the metal halide contains a metal which is selected from Group VIII, Group IB, Group IIB and Group IIIA of the Periodic Table of The Elements.

9. The process of claim 8 wherein the metal halide is selected from the group consisting of a chloride of aluminum, copper, iron, and zinc.

10. The process of claim 1 wherein the ionic liquid composition has a mole ratio of the alkyl-containing amine hydrohalide salt to metal halide of from about 1:1 to about 1:2.5, the metal halide is aluminum trichloride, and the alkyl-containing amine hydrohalide salt is trimethylamine hydrochloride.

11. A process as claimed in claim 1 wherein dodecene is reacted with benzene.

12. A process as claimed in claim 1 wherein dodecene is reacted with benzene, the ionic liquid composition has a mole ratio of the alkyl-containing amine hydrohalide salt to metal halide of from about 1:1 to about 1:2.5, the metal halide is aluminum trichloride, and the alkyl-containing amine hydrohalide salt is trimethylamine hydrochloride.

13. A process as claimed in claim 1 wherein dodecyl chloride is reacted with benzene.

14. A process as claimed in claim 1 wherein dodecyl chloride is reacted with benzene, the ionic liquid composition has a mole ratio of the alkyl-containing amine hydrohalide salt to metal halide of from about 1:1 to about 1:2.5, the metal halide is aluminum trichloride, and the alkyl-containing amine hydrohalide salt is trimethylamine hydrochloride.

15. A process as claimed in claim 1 wherein the reaction uses an alkylating agent carrying a functional group that is substantially nonreactive with the catalyst.

16. A process as claimed in claim 15 wherein the alkylating agent is oleonitrile.

* * * * *